United States Patent [19]

Aubin

[11] 4,163,049

[45] Jul. 31, 1979

[54] COMPOSITION ACTIVE WITH RESPECT TO ERYTHEMA SOLARE

[75] Inventor: Michel F. Aubin, Fougeres Agris, France

[73] Assignee: Societe d'Etudes et de Participation O.H.F., Asnieres, France

[21] Appl. No.: 794,588

[22] Filed: May 6, 1977

[30] Foreign Application Priority Data

May 6, 1976 [FR] France ................ 76 13599

[51] Int. Cl.$^2$ ...................... A61K 7/42; A61K 35/64; A61K 35/78
[52] U.S. Cl. ........................................ 424/59; 424/98; 424/195; 424/DIG. 13
[58] Field of Search ............ 424/59, 195, 98, DIG. 13

[56] References Cited

U.S. PATENT DOCUMENTS 395,824  1/1889  Gentry ................ 424/195

FOREIGN PATENT DOCUMENTS 272664  3/1964  Australia .

OTHER PUBLICATIONS

The Dispensatory of the U.S.A., 24th Ed. (1947), published by J. B. Lippencott Co., Phila. Pa., pp. 1282–1283, 1379–1380.

J. of Ecgromic Entomology, vol. 30, (1973), published by Amer. Assoc. of Econ. Entomologists, Wisc., pp. 41–43.

*Primary Examiner*—Donald B. Moyer
*Attorney, Agent, or Firm*—Sughrue, Rothwell, Mion, Zinn and Macpeak

[57] ABSTRACT

A composition active with respect to erythema solare, which comprises a mixture of tinctures of Apis mellifica at a dilution of from 4° CH to 15° CH and Calendula at a dilution of from a third decimal to 9° CH.

7 Claims, No Drawings

COMPOSITION ACTIVE WITH RESPECT TO ERYTHEMA SOLARE

The present invention relates to a composition active with respect to erythema solare, i.e., having a preventive and/or curative effect on erythema solare.

Erythema solare, commonly called "sunburn" is an inflammation involving the local release in the skin cells of various chemical mediators whose principal constituents are histamine and quinines, the effects of radiation being well known from other sources, cf. for example the case histories in Nouvelle Presse Médicale "Phoebus et les Estivants" (Phoebus and the holiday-makers), Nouvelle Presse Médicale, 1974, No. 28 (20–27 July), pages 1759 to 1776, and A. FOURTANIER, discussion held before the French Society of Cosmetology, Feb. 28, 1974.

The object of the products normally used in cosmetology or even in therapeutics (for example nicotinamide-synthetic antipaludents) is generally to increase protection against solar radiation by increasing the cutaneous pigmentation. The object of the present invention is to prevent and/or treat inflammatory conditions of the skin caused by exposure to solar radiation.

It is well known, and has been confirmed by work carried out by P. and J. BASTIDE and colleagues (Annales Homéopathiques Françaises, 1975, No. 3) that whole bee (*Apis mellifica*) extracts in homeopathic dilutions, whose major constituents are histamine and quinines, stop inflammation conditions.

Moreover, the therapeutic effect of marigold (*Calendula officinalis*) in the treatment of wounds and skin conditions and in particular burns is already known, and work carried out by P. and J. BASTIDE has shown that Calendula has an anti-inflammatory activity, less marked than that of Apis but nevertheless not negligible.

It has now been found that the presence of Calendula potentialises extremely sharply the effect of Apis with regard to erythema solare, both from the preventive and curative aspects.

The present invention thus relates to a composition having a preventive and/or curative effect on erythema solare, which can be administered in particular orally or perlingually, and which comprises a mixture of tinctures of *Apis mellifica* and *Calendula officinalis*.

The present invention provides a composition active with respect to erythema solare, which comprises a mixture of tinctures of *Apis mellifica* at a dilution of from 4° CH to 15° CH and Calendula at a dilution of from a third decimal to 9° CH.

According to the invention, there may be used dilutions of *Apis mellifica* of from a quarter centesimal hahnemann (4° CH) to 15° CH, and dilutions of *Calendula officinalis* of from a third decimal to 9° CH; however, the preferred formulation for oral or perlingual administration is a combination of 7° CH Apis and 4° CH Calendula.

The dilutions of the tinctures of *Apis mellifica* and Calendula may be suitably present in equal parts by weight.

The active components of the composition according to the invention may be incorporated in a suitable excipient used for pharmaceutical preparations, this excipient depending on the method of administration chosen.

In particular, one of the preferred forms is "glossettes" for perlingual use, glossettes being small tablets intended to be placed under the tongue and resorbed slowly thereby; the excipient used may consist of sucrose-lactose or sucrose, lactose and maltose-dextrose, or any other product suitable for this form of administration.

The preparation of the product in the form of glossettes is carried out from stock tinctures by preparing the dilutions, which are then carefully incorporated into the mixture of powders constituting the excipient, preferably in equal parts by weight of the two dilutions. The composition obtained is then compressed to obtain the glossettes.

However, other oral forms may also be used, such as drops, lozenges, pills, ampoules for oral application, syrup or pellets. Moreover, the composition according to the invention may be used in the form of a cream or ointment for cutaneous treatments, the active constituents being incorporated in suitable excipients.

In particular when the composition is used in the form of a cream, it may suitably contain a tincture of 7° CH *Apis mellifica* and a tincture of a third DH Calendula.

As has been mentioned above, the composition according to the invention exhibits its effect on erythema solare both as regards the visible symptoms (redness and swelling) and also as regards palpable symptoms (pain).

On the other hand, the synergistic effect obtained by adding Calendula to Apis has been demonstrated not only as regards its curative activity, but also as regards its protective and preventive activity.

The demonstration of this synergistic effect was first made by means of a series of pharmacological tests carried out on albino guinea-pigs with regard to erythema produced by ultra-violet radiation, by the oral-perlingual administration of the combination Apis 7° CH and Calendula 4° CH. The results obtained were then compared with the results found using a 7° CH Apis preparation on the one hand and a 4° CH Calendula preparation on the other hand.

The principle of the tests is as follows:

An ultra-violet spotlight directed on the abdominal skin of albino guinea-pigs causes an erythema, which is then investigated in the presence of the substance being tested or its excipient alone (placebo). The double blind method of testing is adopted.

The experimental procedure adopted is as follows:

(a) Preparations used

The products being tested consist of a mixture of *Apis mellifica* 7° CH and Calendula 4° CH in purified distilled water sufficient to make up a 1 ml ampoule for oral application.

The placebo consists of purified distilled water in a 1 ml ampoule for oral application.

(b) Choice of animals

The animals used are albino guinea-pigs weighing 350 to 400 g, derived from the same stock, and each experiment comprises 6 batches each of 6 animals.

(c) Choice of equipment

The equipment consists of a 550 watt ultra-violet lamp and a thick black laminated material screen pierced by 4 holes of 1 cm diameter arranged in the form of a square, and whose centres are 3 cm apart.

(d) Operating method

The day before the experiment the guinea-pigs are carefully dehaired in the abdominal region, using a depilatory preparation.

Animals with damaged skin are rejected, and the remaining animals are used to demonstrate the curative activity of the combination.

All the injections of the substances being tested are made oro-perlingually in a volume of 1 ml per animal. The end of the canula fitted to the syringe is placed under the tongue of the animal and the piston is pushed in slowly in small impulses so as to deliver 1 ml per minute.

At time zero, i.e., immediately before irradiation, the first control batch receives an oro-perlingual administration of purified distilled water, and the first treated batch receives under the same conditions and oro-perlingually 1 ml of the 7° CH Apis mellifica 4° CH Calendula preparation.

For the first control of treated batches, the administrations, are repeated at times +15, +30, and +45 minutes.

For the second control of treated batches, the administrations are repeated at times +15, +30, +45 and +240 minutes.

1—Controls: Administration of purified distilled water.

| Time (minutes) | 0 | +15 | +30 | +45 | +240 |
|---|---|---|---|---|---|
| 1st batch 6 animals | | 1 ml | 1 ml | 1 ml | 1 ml |
| 2nd batch 6 animals | | 1 ml | 1 ml | 1 ml | 1 ml | 1 ml |

2—Treated: Administration of 7° CH Apis mellifica and 4° CH Calendula to the same number of animals, the amounts and times being identical to those of the control animals.

| Time (minutes) | 0 | +15 | +30 | +45 | +240 |
|---|---|---|---|---|---|
| 1st batch 6 animals | | 1 ml | 1 ml | 1 ml | 1 ml |
| 2nd batch 6 animals | | 1 ml | 1 ml | 1 ml | 1 ml | 1 ml |

The animals are subjected to the following treatment: The guinea-pigs are lightly anaesthetized with ether, and, after the screen has been placed on the abdominal skin, they are subjected to U.V. irradiation for 1 minute with ventilation in order to bring the temperature of the surrounding region to 30° C. The four "spots" should fall perpendicularly on the cutaneous surface.

(e) Expression of results

The erythema is noted in all cases 4 hours and 24 hours after irradiation, and for each spot:
-0: no erythema
-1: spots just discernible
-2: erythema more marked
-3: erythema very visible.

The maximum score for a guinea-pig is thus 12.

This scoring should be carried out in all cases in an identical manner and under the same lighting conditions.

For this to be so, the abdominal skin of the guinea-pig is gently rubbed four times.

The scores for each animal are added up and the inhibition percentage with respect to the controls is calculated from the formula:

$$P = \frac{(\text{Scores for controls} - \text{scores for treated animals}) \times 100}{\text{Scores for controls}}$$

The results obtained are given in the following tables:

| 1st batch: Controls, 4 hours and 24 hours | | | | | | | |
|---|---|---|---|---|---|---|---|
| No. of animals | 1 | 2 | 3 | 4 | 5 | 6 | Total |
| Score 4 hours after irradiation | 12 | 10 | 12 | 12 | 10 | 12 | 68 |
| Score 24 hours after irradiation | 12 | 10 | 12 | 12 | 10 | 12 | 68 |

| 2nd batch: Controls, 4 hours and 24 hours | | | | | | | |
|---|---|---|---|---|---|---|---|
| No. of animals | 1 | 2 | 3 | 4 | 5 | 6 | Total |
| Score 4 hours after irradiation | 12 | 12 | 12 | 8 | 12 | 12 | 68 |
| Score 24 hours after irradiation | 12 | 12 | 12 | 12 | 12 | 12 | 72 |

| 1st batch: Treated animals, 4 hours and 24 hours | | | | | | | | |
|---|---|---|---|---|---|---|---|---|
| No. of animals | 1 | 2 | 3 | 4 | 5 | 6 | Total | P % |
| Score 4 hours after irradiation | 4 | 8 | 8 | 4 | 8 | 0 | 32 | 52.94% |
| Score 24 hours after irradiation | 2 | 4 | 2 | 2 | 4 | 4 | 18 | 73.52% |

| 2nd batch: Treated animals, 4 hours and 24 hours | | | | | | | | |
|---|---|---|---|---|---|---|---|---|
| No. of animals | 1 | 2 | 3 | 4 | 5 | 6 | Total | P % |
| Score 4 hours after irradiation | 6 | 4 | 4 | 2 | 4 | 4 | 24 | 64.70% |
| Score 24 hours after irradiation | 0 | 2 | 2 | 0 | 4 | 0 | 8 | 88.88% |

From the above experiments it can be concluded that the preparation 7° CH Apis mellifica and 4° CH Calendula has a curative effect with regard to erythema induced in guinea-pigs by U.V. radiation.

Furthermore, this curative effect illustrates the potentialisation of Apis by Calendula on comparison with the results obtained for Apis 7° CH by itself and Calendula by itself (cf. P. and J. BASTIDE and Colleagues, already quoted).

In actual fact, the protective activity percentages are respectively:

| | Calendula 4° CH | Apis Mellifica 7° CH | Apis Mellifica 7° CH + Calendula 4° CH |
|---|---|---|---|
| in 4 hours | 34% | 43% | 53% |
| in 24 hours | 63% | 68% | 73.5% |
| in 4 hours | 34% | 47% | 65% |
| in 24 hours | 68% | 81% | 89% |

Moreover, a series of pharmacological tests was carried out on albino guinea-pigs with regard to erythema produced by ultra-violet radiation, by external use of a cream containing 7° CH Apis in association with 3° DH Calendula.

The principle of the tests is as follows.

The day before the test, the guinea-pigs are dehaired at their abdominal region and then put in single cages without food but they could drink at will.

A batch of 6 animals is used for each application of the composition being tested. The composition is administered by local application until it penetrates the skin by gentle massage.

After a quarter of an hour, the animals are exposed to ultra-violet radiation for 60 seconds and examined after 4 hours and 24 hours from irradiation.

The abdominal skin of the animals is gently rubbed 4 times. The erythema is marked 0 to 3.

The scores for each batch are added up and the inhibition percentage with respect to the controls is calculated from the formula:

$$P = \frac{(\text{Scores for controls} - \text{scores for treated animals}) \times 100}{\text{Scores for treated animals}}$$

The results obtained are as follows:

1st batch: Controls The guinea-pigs are dehaired the day before and receive nothing.

| Animal No. | Score 4 hours after irradiation | Sum | Score 24 hours after irradiation | Sum |
|---|---|---|---|---|
| 1 | 3 | 12 | 3 | 12 |
| 2 | 3 | 12 | 3 | 12 |
| 3 | 3 | 12 | 3 | 12 |
| 4 | 3 | 12 | 3 | 12 |
| 5 | 3 | 12 | 3 | 12 |
| 6 | 3 | 12 | 3 | 12 |
| Total | | 72 | | 72 |

2nd batch: Treated animals - The animals are dehaired the day before and received an excipient called CETALINE 15 minutes before exposure to ultra-violet radiation.

| Animal No. | Score 4 hours after irradiation | Sum | Score 24 hours after irradiation | Sum |
|---|---|---|---|---|
| 7 | 3 | 12 | 3 | 12 |
| 8 | 3 | 12 | 3 | 12 |
| 9 | 3 | 12 | 3 | 12 |
| 10 | 3 | 12 | 3 | 12 |
| 11 | 3 | 12 | 3 | 12 |
| 12 | 3 | 12 | 3 | 12 |
| Total | | 72 | | 72 |

It was noted that there was no difference between the controls and the animals treated with CETALINE.

3rd batch of animals treated with the cream to be tested:

The cream used has the following composition:

| 7° CH Apis mellifica | 2 g |
|---|---|
| 3° DH Calendula | 2 g |
| Cetaline, quantity sufficient for | 100 g |

The animals dehaired the day before receive an application of cream 15 minutes before exposure to ultra-violet radiation.

| Animal No. | Score 4 hours after irradiation | Sum | Score 24 hours after irradiation | Sum |
|---|---|---|---|---|
| 13 | 0 | 0 | 0 | 0 |
| 14 | 1 | 4 | 0 | 0 |
| 15 | 0 | 0 | 0 | 0 |
| 16 | 0 | 0 | 0 | 0 |
| 17 | 1 | 4 | 0 | 0 |
| 18 | 0 | 0 | 0 | 0 |
| Total | | 8 | | 0 |

The percentages of protection activity are, respectively, 88-89% for the batch treated 4 hours after irradiation and 100% for the batch treated 24 hours after irradiation.

In conclusion, the cream tested has a remarkable protection activity against erythema due to ultra-violet radiation with guinea-pigs, whereas the excipient alone of the cream shows no activity.

Moreover the activity of the composition according to the invention has been demonstrated in man, both as a preventative effect obtained by taking 2 glossettes morning and evening to obtain protection against sunburn, and as a curative effect to alleviate an already existing and not preventively treated sunburn, by taking 2 glossettes every half hour.

This action on erythema solare in man is shown by the following clinical case histories:

Case I: Madame D. D. . . . , age 40, exhibited an erythema solare of the dorsal region. The skin was uniformly red and there was a high burn and injection type pain level. On taking the composition in an amount of 2 glossettes every half hour, the pain very rapidly receded and recovery occurred in 24 hours.

Case II: Monsieur R. D. . . . , age 27, exhibited a marked erythema solare of the face and in particular of the nose and eyelids, which were red and swollen, with sharp burn type pains. On taking the composition in an amount of 2 glossettes every half hour, the condition of the illness improved extremely rapidly.

Case III: A clinical experiment was carried out by a group during skiing instruction in February. A prophylactic dosage of 2 glossettes of the composition morning and evening for the weeks before the instruction considerably reduced the incidence of sunburn with respect to the other groups.

Case IV: A similar clinical experiment was carried out by two groups during sailing in July. The frequency of solar erythemas among the individuals in the first group who were treated by application of a cream prepared in accordance with the formula indicated above was almost nil, whereas in the second group formed by non-treated persons it attained 70%.

Case V: Monsieur J. L. . . . , age 30, very often suffered sunburn during the holiday period. A regular dosage of the composition in the form of 2 glossettes morning and evening enabled him to spend his holidays at the seaside without any anxiety.

Clinical experimentation of the composition on a species of animals and then on a large number of patients have shown moreover that the composition is entirely free from any toxic or secondary effects.

We claim:

1. A composition active with respect to erythema solare, which comprises synergistic a mixture of tinctures of *Apis mellifica* at a dilution of from 4° CH to 15° CH and Calendula at a dilution of from a third decimal to 9° CH.

2. A glossette to be administered orally comprising, a synergistic mixture of a tincture of 7° CH *Apis mellifica* and a tincture of 4° CH Calendula incorporated in a suitable excipient.

3. A glossette according to claim 2, wherein said dilutions of tinctures of *Apis mellifica* and Calendula are used in equal parts by weight in the excipient.

4. A process for the prophylactic treatment of erythema solare which comprises administering in an amount of one to five glossettes per day the glossette of claim 2.

5. A process to treat erythema solare which comprises administering in an amount of one to three glossettes every half hour the glossette of claim 2.

6. A cream to be administered cutaneously comprising a synergistic mixture of a tincture of 7° *Apis mellifica* and a tincture of Calendula at a third decimal hahnemann incorporated in a suitable excipient.

7. A cream according to claim 6, wherein said dilutions of tinctures of *Apis mellifica* and Calendula are used in equal parts by weight in the excipient.

* * * * *